United States Patent
Halevie-Goldman

(12) 
(10) Patent No.: US 7,985,737 B2
(45) Date of Patent: *Jul. 26, 2011

(54) COMPOSITIONS AND METHODS FOR THE REGULATION OF HOMOCYSTEINE LEVELS WITHIN THE BODY

(75) Inventor: Brian D. Halevie-Goldman, Walnut Creek, CA (US)

(73) Assignee: Fast Balance, Inc., San Rafael, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 12/238,586

(22) Filed: Sep. 26, 2008

(65) Prior Publication Data

US 2009/0239826 A1 Sep. 24, 2009

Related U.S. Application Data

(63) Continuation of application No. 11/043,538, filed on Jan. 26, 2005, now Pat. No. 7,429,569.

(60) Provisional application No. 60/540,029, filed on Jan. 29, 2004.

(51) Int. Cl.
*A01N 43/04* (2006.01)
*A61K 31/70* (2006.01)

(52) U.S. Cl. ............... 514/23; 514/42; 514/43; 514/45; 514/48; 514/49; 514/52

(58) Field of Classification Search .................. None
See application file for complete search history.

(56) References Cited

U.S. PATENT DOCUMENTS

| 5,716,941 A * | 2/1998 | Rabinoff | 514/52 |
| 5,922,704 A * | 7/1999 | Bland | 514/185 |
| 6,503,947 B1 * | 1/2003 | Lipton et al. | 514/575 |

OTHER PUBLICATIONS

Vlasveld "Low cobalamin (vitamin B12) levels in multiple myeloma: a retrospective study" (2003), Van Zuiden Communications.*
Jenkins et al. Am. J. Clin. Nutr. (2002), vol. 76, pp. 365-372.*

* cited by examiner

*Primary Examiner* — Patrick Lewis
(74) *Attorney, Agent, or Firm* — Seyfarth Shaw LLP; John C. Serio

(57) ABSTRACT

Described herein is a method for reducing levels of the harmful metabolic waste product of S-adenosylmethionine (SAMe), homocysteine, and provide vitamin and other nutritional co-factors that reduce the production of homocysteine and either re-methylate homocysteine back to S-adenosylmethionine, or facilitate its conversion downstream to cystathione. The method of the invention may be achieved by administering 5-methyl tetrahydrofolate, methylcobalamin, and one or more compounds selected from the group consisting of betaine, pyridoxal-5-phosphate, N-acetyl-cysteine, and other cofactors.

30 Claims, No Drawings

COMPOSITIONS AND METHODS FOR THE REGULATION OF HOMOCYSTEINE LEVELS WITHIN THE BODY

CROSS-REFERENCE TO RELATED APPLICATIONS

This application claims the benefit of provisional patent application U.S. Ser. No. 60/540,029, filed Jan. 29, 2004 by the present inventor.

FIELD OF THE INVENTION

Embodiments of the present invention are directed to reducing levels of the harmful metabolic waste product of S-adenosylmethionine (SAMe), homocysteine, and provide vitamin and other nutritional co-factors that reduce the production of homocysteine and either re-methylate homocysteine back to S-adenosylmethionine, or facilitate its conversion downstream to cystathione. The formulations disclosed herein may be used to treat conditions contrary to good mental health, heart disease, and cerebrovascular disease, and to promote and maintain the health of the body.

BACKGROUND OF THE INVENTION

Of all the reactive transitional metabolites that are potentially toxic per se, or combine with naturally occurring chemical moieties to produce harmful substances, homocysteine is one of the most relevant and important for human health and disease. Its elevation correlates highly with some of the most prevalent human illnesses, including cardiovascular disorders, renal failure, psychiatric disorders and cognitive impairment, pregnancy complications and birth defects (Refsum. H. et al. (2004) Clin Chem. 50:3-32).

Homocysteine is formed by demethylation of the essential amino acid, methionine. In the cell, methionine is partitioned between protein synthesis and the formation of S-adenosylmethionine (SAMe). SAMe is the most central methylating agent in the cell, and the only methyl donor in the central nervous system. The product of methylation reactions involving SAMe is S-adenosylhomocysteine (SAH), which is reversibly hydrolyzed to homocysteine. In most tissues, homocysteine may be remethylated to methionine, and hence to SAMe, by the enzyme methionine synthase (MS). This reaction requires vitamin B12 as a cofactor and methyltetrahydrofolate as substrate. In certain tissues, mainly liver and kidney, the enzyme betaine homocysteine methyltransferase (BHMT) provides an alternate pathway for the remethylation of homocysteine to SAMe, using betaine as a substrate. In the transsulfuration pathway, homocysteine may be condensed irreversibly with serine to cystathionine and cysteine in two vitamin B6-dependent reactions. Cysteine is a precursor of glutathione (GSH), the major redox buffer in the cell. For further review of homocysteine metabolism pathways, see Selhub, J. (1999) Annu. Rev. Nutr. 19:217-246; Finkelstein, J. D. (2000) Seminars in Thrombosis and Hemostasis 26:219-225; Kruger, W. D. (2000) Vitamins and Hormones 60:333-352.

In the metabolic pathways, homocysteine sits downstream of the most central methylating agent, S-adenosylmethionine (SAMe), and it sits upstream of some very common bottlenecks or blockages in the metabolic pathways. These blockages could take the form of genetic polymorphisms affecting enzymes in this pathway, or the pathway of its co-enzymes, such as folate metabolism. Alternatively, upstream accumulation of homocysteine might reflect a nutritional deficiency, life style factors or other strains to the homeostatic mechanisms that regulate the metabolic pathways.

Homocysteine itself is a toxic waste product, and not merely an indicator of a road block in the methylation—remethylation cycle. Homocysteine may be converted to the reactive toxin, homocysteine-thiolactone (see Jacubowski, H., and Goldman, E., (1993) FEBS Lett. 317:237-240).

SAMe, the product of homocysteine re-methylation, regulates gene expression and helps prevent genetic mutations; it maintains mitochondrial function; it participates in phospholipid synthesis and maintains the integrity of cell membranes; and it regulates neurotransmitters such as serotonin, dopamine and epinephrine (adrenaline), and hormones such as estrogen and melatonin.

Administering SAMe to subjects has been found to have a variety of salutary effects. U.S. Pat. No. 5,166,328 and U.S. Application No. 2002/0025926, the disclosures of which are incorporated herein by reference, describe some of these effects in the brain: it inhibits neuron death following ischemia; it improves the utilization of glucose in the brain; it inhibits brain edema; it improves EEG and evoked potential findings by normalizing them; and it improves motor function, such as that impaired by stroke. SAMe has been found, for example in meta-analyses of multiple drug studies, to enhance emotional well-being and is as effective as many common prescription drugs—tricyclics such as Elavil® (amitriptyline HCl) and Norpramin® (desipramine hydrochloride), and Selective Serotonin Reuptake Inhibitors (SSRIs) such as Prozac® (fluoxetine hydrochloride), Zoloft® (sertraline hydrochloride), and Paxil® (paroxetine hydrochloride)—in treating depression, but with significantly fewer side effects than any of these drugs. SAMe has also been used to treat anxiety, chronic pain, arthritis, rheumatoid fibromyalgia, Chronic Fatigue Syndrome, cognitive difficulties associated with Alzheimer's Disease, neurovascular disease and neurological conditions associated with AIDS. In addition to diseases of the central and peripheral nervous system, SAMe has been found to improve diseases of the joints, cardiovascular system, and liver.

Administering compounds that decrease homocysteine to subjects has been found to have a variety of salutary effects. Anti-homocysteine agents have been used to treat cognitive and neurological disorders, including senile dementia and depression (Godfrey, P. S. A. et al. (1992) Br. J. Psychiatry 161:126-127) and cardiovascular disorders such as atherothrombotic cerebrovascular disease, (Verneulen, E. G. et al., (2000) Neth. J. Med. 56:138-146).

SUMMARY OF THE INVENTION

It is an object of the invention is to reduce the harmful metabolic waste product of SAMe, homocysteine. Described herein is a method of decreasing levels of homocysteine within the body by providing vitamin and other nutritional co-factors that reduce the production of homocysteine and either re-methylate homocysteine back to S-adenosyl-methionine, or facilitate its conversion downstream to cystathione. This may be accomplished by increasing levels of cofactors and substrates required for re-methylation of homocysteine to SAMe and/or increasing levels of cofactors and substrates required for transsulfation of homocysteine to cysteine.

A further object of the invention is to provide nutrients that steer the metabolic pathways away from the production of homocysteine, by decreasing the metabolic stresses that require the diversion of SAMe to produce other products. This may be accomplished in several ways: (1) Increase levels of the important anti-oxidant, glutathione (GSH). Provision of other anti-oxidants reduces the body's requirements for glutathione. These anti-oxidants may include, for example, vitamins A, C and E, the element zinc, and other known anti-oxidants. Glutathione may be administered but it is hardly absorbed (although it has some benefit locally in the gut). However, a precursor of glutathione, N-acetyl-cysteine, may be added. (2) Increase methylation substrates and cofactors. These may include, for example, betaine (also known as trimethyl-glycine, or TMG), folic acid (preferably in the methyl form, 5-methyl-THF) and vitamin B12 (preferably in the methyl form, methylcobalamin). Dimethyl-thetin is another naturally occurring methylated substrate that in the process of losing a methyl group tends to remethylate homocysteine to methionine. Allicin (from garlic) functions in a similar fashion to TMG and trimethyl-thetin, and is also a sulfation substrate. (3) Increase sulfation substrates and cofactors. These may include, for example, N-acetyl-cysteine and allicin (from garlic), as well as L-taurine.

In an embodiment of the invention, the method comprises administering to a subject 5-methyltetrahydrofolic acid (5M-THF), methylcobalamin, and one or more of betaine, pyridoxal-5-phosphate (P5P), N-acetyl-cysteine, and other cofactors. In one embodiment, the composition comprises all of these compounds (5M-THF, methylcobalamin, betaine, P5P, and N-acetyl-cysteine). The composition may contain at least one co-factor such as, but not limited to, a B-vitamin, Intrinsic Factor, piperine, alpha-lipoic acid, choline bitartrate, selenomethionine, a sulfur-containing amino acid, such as N-acetyl cysteine and taurine, a mineral such as calcium and magnesium, an antioxidant, and a phytonutrient. According to one method of the invention, the subject ingests during one part of the day, such as the morning, a first formulation containing 5M-THF, methylcobalamin, and one or more of betaine, P5P and N-acetyl cysteine, and ingests during another part of the day, such as the evening, a second formulation comprising co-factors that are balancing, calming and leveling in contrast to the more energizing morning product. Any of the foregoing methods and compositions may be supplemented by the addition of the anxiolytic anti-convulsant mood-stabilizers kava kava and/or GABA, two compounds which further increase the beneficial effects and improve the safety of SAMe, the product of remethylation of homocysteine. Since a hyper-methylated state, induced by SAMe, may in theory exacerbate a bipolar disorder state, and may be associated with a pro-convulsant effect in epileptic conditions, the addition of these natural anti-convulsant mood stabilizers may be useful.

In order to provide all available safety measures to potential users of other products, one has to consider that the facilitation of methylation is not necessarily beneficial in two particular situations. Firstly, a state of over-methylation or a hypermethylated state may occur in the manic phase of a bipolar disorder or a florid schizoaffective psychotic state. Either those diagnosed or at risk for these conditions might be forewarned to avoid the compositions of the invention, or anti-convulsant mood-stabilizing ingredients may be added to diminish this risk. Substances such as kavain, dihydroxy-kavaine, methysticin, dihydro-methysticin, yangonin and desmethoxy-yangonin, and other kava lactones in the herb, Kava, inhibit voltage-dependent sodium and calcium channels and have a GABA-A agonistic and an anti-glutamate action, and raise the seizure threshold and have a mood-modulatory action. Secondly, the methylation of membrane phospholipids, where only low-quality and rigid saturated fatty acids are available for methylation and are therefore incorporated in neuronal receptor membranes rather than the more flexible, unsaturated free-fatty-acids (FFAs), may not well serve the adaptability of the receptor macro-molecular system to optimally adjust to changes in neurotransmitter flow.

It is an object of the invention to provide a method of treating and preventing diseases selected from the group consisting of conditions contrary to good mental health, heart diseases, cerebrovascular diseases, and renal disorders, comprising administering to a human a formulation comprising 5-methyl tetrahydrofolate, methylcobalamin, and one or more compounds selected from the group consisting of betaine, pyridoxal-5-phosphate, and N-acetyl-cysteine.

It is a further object of the invention to provide a method of decreasing homocysteine in a human having a particular genomic configuration, comprising administering to the human a formulation comprising 5-methyl tetrahydrofolate, methylcobalamin, and one or more compounds selected from the group consisting of betaine, pyridoxal-5-phosphate, and N-acetyl-cysteine.

DETAILED DESCRIPTION OF THE INVENTION

The method of the invention may be achieved by administering compositions comprising 5-methyl-tetrahydrofolic acid (5M-THF) and methylcobalamin, together with at least one compound selected from the group consisting of betaine, pyridoxal-5-phosphate (P5P), N-acetyl-cysteine, and other cofactors. All of these compounds are readily available from a wide variety of commercial sources.

In one embodiment of the invention, the method comprises administering to a subject a formulation comprising 5M-THF and methylcobalamin. In a further embodiment, the formulation comprises 5M-THF, methylcobalamin, and at least one compound selected from the group consisting of betaine, pyridoxal-5-phosphate, and N-acetyl-cysteine. In a further embodiment, the composition comprises 5M-THF, methylcobalamin, betaine, pyridoxal-5-phosphate, and N-acetyl-cysteine.

5M-THF: In many cases the presence of a high blood level of homocysteine represents a failure of the remethylation of homocysteine, due to a deficiency of a B vitamin such as folate or B12. This would lead to inadequate production of a critically important anti-oxidant, the tri-peptide glutathione, the absence of which would render the body vulnerable to a variety of oxidative stresses. Homocysteine itself is a toxic waste product, and not merely an indicator of a road block in the methylation—remethylation cycle. Homocysteine may be converted to the reactive toxin, homocysteine-thiolactone (see Jacubowski, H., and Goldman, E., (1993) FEBS Lett. 317:237-240). In any case, it is useful to ensure adequate quantities of the methylation co-factors, such as folate and vitamin B12, and betaine (also known as trimethyl-glycine (TMG)), which in the course of being converted to DMG (Di-Methyl-Glycine), shifts the metabolic current away from the beaching of metabolic driftwood, such as homocysteine.

SAMe is needed for the synthesis of tetrahydrobiopterin (BH4), a component of folic acid, which is an essential co-enzyme for the synthesis of what might be called the 'feel-good' monoamines, serotonin and dopamine. Most recurrently depressed individuals have been shown to have low levels of BH4, probably as a result of low SAMe levels, and in these individuals, the provision of BH4 results in remarkable improvement. BH4 is expensive and unstable, and has not been considered a commercially marketable proposition, since the body makes it readily given sufficient folic acid, vitamin B12 and vitamin C. For this purpose, folate may be needed in very high doses unless a proportion of this coenzyme is supplied in the 5-methyl-form.

There is a fairly common genetic variant or polymorphism, which results in the relative inactivity of the enzyme that converts folic acid to its active methyl form. The enzyme known as 5,10 methylene tetrahydrofolate reductase, (MTHFR), aided by the methyl form of vitamin B12, creates 5-methyl-terahydrofolate (5-methyl-THF). The prevalence of the genetic MTHFR polymorphisms, such as the C677T and the A1298C polymorphisms, which affect the MTHFR enzyme has been reported to be from about 12% to as much as 40% of the population. It is this methyl form of folic acid, created with the help of this enzyme, which is responsible for the all-important remethylation of homocysteine back to methionine.

Now a critical problem arises when SAMe is present in high concentrations in the body. There is a feedback mechanism whereby SAMe inhibits the MTHFR enzyme, the very same enzyme whose activity may be compromised in so many genetically vulnerable people. Therefore, to obtain increased benefits and safety for the compositions of the invention, at least a proportion of the folic acid provided in the compositions of the invention is preferably in the pre-activated methyl form, 5M-THF, to bypass this metabolic bottleneck.

Some non-methylated forms of folic acid are needed for other purposes, e.g. DNA synthesis, and these much less costly forms of folate are useful inclusions in the compositions of the invention as well. (With respect to dosage, Abbott has shown that 2.5 mg of folate gives similar results to 10 mg of folate).

Methylcobalamin: There is a danger to a product that provides the active form of folic acid or vitamin B11 that does not also ensure adequate amounts of vitamin B12. Both vitamin B11 (folate) and B12 deficiency may cause the hematological condition known as macrocytic anemia. That implies that the diminished number of circulating red blood cells (RBCs) have a larger mean cell volume (MCV) and have a larger mean concentration of hemoglobin (MCH). If a B12 deficiency is present in a mild form or a severe condition known as pernicious anemia, serious irreversible neurological complications are likely to develop. Should the macrocytic anemia be treated with Vitamin B11 (folic acid) and not B12, the hematological problems would likely improve but the neurological complications would get worse. Therefore, in many cases, indiscriminant treatment with vitamin B11 (or folic acid) without vitamin B12 might mask the diagnostically important macrocytosis and exacerbate underlying neuropsychiatric illness. This is potentially even more of a problem when the 5-Methyl-THF form of folate is utilized, since the pteridine, methylene and other forms of folic acid (other than 5-methyl-folate) are needed for other important metabolic processes. Absent available vitamin B12, the folic acid might get locked in its methyl form, and be unavailable for its other important metabolic roles.

Given the importance of folic acid, the methyl form of folic acid, and the need to ensure sufficient quantities of vitamin B12, it is useful to clarify the form of vitamin B12 that is preferably included in the compositions of the invention. It is desirable to include methylcobalamin, the methyl form of vitamin B12, in addition to the usual form of B12, which is cyanocobalamin. This is because the methyl form is much more easily absorbed in the gut, and has much better penetration across the blood-brain-barrier (BBB). The methyl form of vitamin B12 is extremely expensive, however, only very small quantities are needed to ensure adequate amounts reach their target sites. The complex absorption mechanisms for vitamin B12, and the problems that occur not uncommonly in vegetarians, elderly people, those taking antacids, and those with various gastrointestinal conditions are well known to the medical profession and those conversant with the art. To provide compositions for a broad base of the population, including a subset that might potentially have a multitude of co-morbid conditions, the presence of adequate amounts of vitamin B12 at critical target sites in the body, for example, the brain, is preferably assured.

For reasons of clinical efficacy as well as economy, the ratio of B12 in its more economical cyanocobalamin form to its methylcobalamin form is preferably between 5:1 and 50:1. An example of a preferred embodiment has a ratio of 10:1. Similarly, for much the same reasons, vitamin B11, more commonly known as folate or folic acid, is preferably present in a ratio of the folate form to the 5-methyl-terahydrofolate form of between 5:1 and 50:1, more preferably 10:1.

Intrinsic factor (IF) is a glycoprotein that plays an important role in the absorption of vitamin B12. Given sufficient quantities of stomach acid, it is secreted by the gastric parietal cells, and it facilitates absorption of B12 further down the gut in the terminal ileum. Addition of Intrinsic Factor may provide additional insurance that sufficient B12 is absorbed into the circulation, so that alternative routes of administration (such as intramuscular or sublingual) would not be necessary. IF is commercially available as an extract from the digestive tracts of pigs or cows. Therefore, the compositions of the invention in their various embodiments may include IF.

It is known, however, that if an organism consumes sufficient B12 in the diet, there is a so-called 'mass action' effect, whereby a certain portion of B12 will be absorbed from the gut into the circulation, despite low amounts or the absence of Intrinsic Factor.

Betaine (also known as Trimethylglycine) donates a methyl group to homocysteine, remethylating it to methionine, thereby preventing homocysteine levels from becoming elevated. Therefore, as betaine (TMG) is converted to dimethyl-glycine (DMG), it shifts the metabolic pathway away from homocysteine. There is substantial research demonstrating the effectiveness of TMG in lowering homocysteine levels, alone or in combination with folate and B12. Several studies show that Folic acid lowers homocysteine more than betaine, but it does not lower it after a methionine load, whereas betaine does, according to Steenage et al., (2003; J. Nut. 133:1291-1295). Therefore, the addition of betaine is important, especially when used in conjunction with the invention described in copending U.S. Patent Application 2002/0025926.

N-Acetyl-Cysteine can be considered a precursor of GSH (reduced glutathione). Cysteine is not an essential amino acid, as it can be produced from methionine via S-adenosyl-homocysteine and homocysteine. Providing cysteine in the diet or in a dietary supplement lowers body requirements for methionine. Cysteine is a good chelating agent and is useful for detoxification, but has a distinctive odor, and is easily prone to degradation. The N-acetylated form of cysteine is more stable, has less of an odor, and may be a more efficient precursor of the body's most important anti-oxidant, glutathione.

SAMe is preserved for its other functions if it is not under oxidative pressure to convert to glutathione. Antioxidants decrease the need for the conversion of SAMe to the powerful anti-oxidant, glutathione, by providing alternative nutritional anti-oxidants. Of the broad range of anti-oxidants that may be included in the compositions of the invention, to decrease the channeling of SAMe to glutathione, the preferred ones include vitamins C and E (predominantly alpha tocopherols, but gamma-tocopherols help preserve vitamin C), vitamin A, the Omega-3 free fatty acids (from fish oils or flax seed oil), anthrocyanidins (from grape seeds or Pycnogenol, from French Pine bark) and certain phytonutrients. There are particular phytonutrients that enhance the respiratory process of the Krebs Cycle even in the absence of adequate oxygenation; these derive from certain plants that have adapted to survive at high elevations where the partial pressure of oxygen is very low.

The most plausible explanation as to why N-acetyl-cysteine would lower homocysteine levels is provided by Ventura et al (1999; Pharmacol. Res. 40:345-350, who suggest that the toxicity of homocysteine (Hcy) seems largely sulphydryl-mediated. Accordingly, the formation of a stable chemical adduct with the free thiol would theoretically prevent generation of thiol-dependent free radicals and the conversion of homocysteine to its oxidized toxic derivatives. There have been some observations in the literature about the possible effects of oral N-acetylcysteine (NAC) on thiol plasma levels, and particularly about a possible effect of reducing total homocysteine plasma levels and modifying the ratio between its different circulating forms (free, protein-bound and reduced forms). In these reports, different hypotheses were made about the mechanism by which NAC exerted its effect. It has been Dr. Ventura's intention to evaluate the effect of IV NAC on plasma thiol levels focusing on the alterations of absolute and relative forms of plasma thiol on the induction of higher urinary excretion, and on the formation of the mixed disulfides, NAC-Hcy, equivalent to the formation of a more stable homocysteine adduct). Basically, according to Ventura et al, NAC increases the renal clearance of homocysteine (and cysteine), supposedly by displacing homocysteine from plasma binding sites and forming mixed disulfides.

Pyridoxal-5-phosphate: Pyridoxine or vitamin B6 is the cofactor for the enzyme cystathione-beta-synthetase, which converts homocysteine to cystathione and then to cysteine. Pyridoxyl-5-phosphate (P5P) is the active form of this co-enzyme or co-factor. Thus the various compositions of the invention may utilize vitamin B6 in addition to P5P.

Chronic inflammation causes an increased production of interleukin-6 (IL-6), which induces pyridoxyl phosphatase activity. Increased pyridoxal phosphatase activity converts the active form of vitamin B6, P5P back to its inactive form, pyridoxine. P5P is the critical co-factor for the transsulfuration enzymes (such as cystathione-beta-synthetase), which convert homocysteine to cystathione, which is then converted to cysteine.

Co-Factors

Compositions of the invention preferably contain at least one co-factor. As used herein, the term "co-factor" refers to those compounds that are important in the methylation process, the sulfation process, or as anti-oxidants. Preferred co-factors include, but are not limited to, alpha-lipoic acid, calcium, magnesium, coenzyme $Q_{10}$, piperine, choline bitartrate, selenomethionine, L-taurine, trimethyl-thetin, allicin (from garlic), zinc, vitamin A, vitamin C, vitamin E, B Complex vitamins, and phytonutrients, that is, extracts from certain plants that have adapted to survive at high elevations (e.g., above 16,000 feet), including, for example, *Eleutherococcus senticosus* (Siberian Ginseng), *Rhododendron caucasium*, and certain of the *Rhodiola* species, such as *Rhodiola rosea, Rhodiola smythii* and *Rhodiola himalensis*. An extract of *Rhodiola Rosea* that is particularly rich in the phenylpropanoid, rosavin, would be one of the more suitable for this purpose.

The B Complex vitamins include the hemapoietic vitamins, folic acid and B12 (in the form of methylcobalamin or hydroxycobalamin), and the energy-releasing vitamins B1 (thiamine) B2 (riboflavin), B3 (in the form of niacin or nicotinic acid or in the form of nicotinamide), B5 (pantothenate), B6 (pyridoxine) and biotin. Biotin is strictly speaking not an essential vitamin, and it is noteworthy that SAMe is required for the methylation reactions involved in the synthesis of biotin.

These and other co-factors are listed below in Table 1. Any of the co-factors listed may be provided as their pharmaceutically acceptable salts.

| COFACTOR | PREFERRED DOSE | DOSE |
|---|---|---|
| Calcium Citrate | 120 mg | 0-500 mg |
| Alpha-lipoic acid | 30 mg | 0-500 mg |
| Thiamine (Vitamin B1) | 1.5 mg | 0-2 mg |
| L-Serine | 50 mg | 0-300 mg |
| Manganese Picolinate | 1.5 mg | 0.0-2 mg |
| Riboflavin (Vitamin B2) | 10 mg | 0-10 mg |
| Biotin | 200 mcg | 0-400 mcg |
| Bioflavenoids (e.g. Quercetin) | 100 mg | 0-500 mg |
| Vitamin C | 100 mg | 0-600 mg |
| Chromium as GTF-chromium | 200 mcg | 0-200 mcg |
| Choline Bitartrate | 10 mg | 0-150 mg |
| Vitamin E Succinate (alpha tocopherol) | 800 IU | 0 IU-1,200 IU |
| Vitamin E (mixed tocopherols, e.g., gamma-tocopherol) | 800 IU | 0 IU-1,200 IU |
| L-Glutamine | 500 mg | 0-1,000 mg |
| Vitamin B3 as niacin or nicotinic acid | 20 mg | 0-200 mg |
| Vitamin B3 as niacinamide | 20 mg | 0-200 mg |
| CoEnzyme Q10 | 60 mg | 0-60 mg |
| Piperine | 6 mg | |
| L-Lysine | 100 mg | 0-500 mg |
| L-Threonine | 500 mg | 0-2000 mg |
| Selenomethionine or kelp extract | 200 mcg | 0-300 mcg |
| Zinc Methionate or Monomethionine | 15 mg | 0-20 mg |
| Omega-3 Free Fatty Acids | 4 g | 0-15 g |

All doses stated above are expressed as daily doses. Doses for the principal active ingredients are set forth below in Table 2.

| COMPOUND | PREFERRED DOSE | DOSE |
|---|---|---|
| 5M-THF | 100 mcg | 0-1,000 mcg |
| Methylcobalamin | 100 mcg | 0-500 mcg |
| Intrinsic Factor | 10 mg | 0-100 mg |
| Betaine | 200 mg | 0-10,000 mg |
| N-acetyl-cysteine | 60 mg | 0-200 mg |
| Pyridoxine (Vitamin B6) | 100 mg | 0-1,000 mg |
| Pyridoxal-5-phosphate | 25 mg | 0-1,000 mg |

As with Table 1, all doses are expressed as daily doses. In one preferred embodiment, the principal active ingredients of Table 2 and the co-factors of Table 1 are administered at a dose of approximately 3,000 mg total principal active ingredients and co-factors a day. This dose is preferably administered in two equivalent doses per day (that is, in two 1,500 mg doses).

The foregoing ingredients are those that steer the metabolic pathways away from the production of homocysteine, by decreasing the metabolic stresses that require the diversion of SAMe to produce other products by: (1) Increasing levels of the important anti-oxidant, glutathione (GSH), by providing alternative anti-oxidants to reduce the body's requirements for glutathione; (2) Increasing methylation substrates and cofactors; and/or increasing sulfation substrates and products.

Coenzyme Q10 (CoEQ10) is a membrane stabilizer and a free radical scavenger that preserves myocardial Na-K ATPase activity and stabilizes myocardial calcium-dependent ion channels. Its metabolite, ubiquinol, prolongs the anti-oxidant effect of the tocopherols (vitamin E) and the tocotrienes. The tocopherols and tocotrienes preserve the thiol groups of glutathione. Should more homocysteine be remethylated to methionine, there would be less cysteine for de novo glutathione synthesis, so that reconstituting and maintaining existing glutathione stores becomes more important.

CoE-Q10 deficiency, already a common problem, is becoming more a problem as the HMG-reductase, cholesterol-lowering statins (e.g. ZOCOR, LIPITOR) become more and more popular. (See study by A K and S A Goli, 2002).

Piperine in a daily dose of 5-6 mg is useful for increasing absorption and increasing plasma levels of (the extremely expensive nutrient) coenzyme Q10.

Choline is a methyl donor, a precursor of the neurotransmitter, acetylcholine.

B-vitamins and other co-enzymes promote the Krebs (Citric Acid) Cycle. The B Complex vitamins include the hemapoietic vitamins, folic acid and B12 (in the form of methylcobalamin or hydroxycobalamin), and the energy-releasing vitamins B1 (thiamine) B2 (riboflavin), B3 (in the form of niacin or nicotinic acid or in the form of nicotinamide), B5 (pantothenate), B6 (pyridoxine) and biotin. Biotin is strictly speaking not an essential vitamin, and it is noteworthy that SAMe is required for the methylation reactions involved in the synthesis of biotin. Riboflavin (vitamin B2) is a co-factor for the folate activation (methylation) enzyme system.

Alpha-lipoic acid and N-acetyl-cysteine decrease the requirements for SAMe with respect to its transsulfuration pathway by providing other sulfur-containing substrates and co-factors. It can regenerate endogenous anti-oxidants, vitamin C and reduced glutathione. In combination with vitamin E it is likely to prevent oxidative stress in cardiac ischemia-reperfusion injury.

Calcium and magnesium, which are essential macronutrients, are frequently inadequately represented in the diet of many individuals, especially those of mature years. Calcium and magnesium have multiple roles in many metabolic pathways, especially the Krebs Cycle. The lack of calcium is likely to contribute to lack of vitamin B12 absorption. Magnesium supplementation is also important. Magnesium should be in a chelated form, so as to diminish the competitive effect of calcium for absorption. An increased concentration of homocysteine causes abnormal magnesium metabolism in cerebral vascular smooth muscle cells (Li W et al. 1999). They are provided in a ratio of by weight of calcium to magnesium of about 1:2 to about 2:1. In an especially preferred embodiment, they are provided in a ratio of about 2 parts calcium to 1 part magnesium.

L-taurine helps mitigate the effects of a possible build up of polyamines, as a result of SAMe metabolism. Polyamines may increase the chances of an arrhythmia, and a composition directed at lowering the polyamines (spermine, spermidine and putrescine), would likely have anti-arrhythmic properties. L-taurine contributes to stabilizing mood, and adds to the hepatoprotective actions of natural SAMe by being part of the sulfation detoxifying process and providing a substrate for tauroconjugation.

Zinc is a physiological antagonist of copper, excessive levels of which are known to raise homocysteine.

Vitamin C in the form of ascorbate, secreted in the gastric lumen, reduces the degraded oxidized form of methyl-folate, 5-methyl-5,6-dihydrofolate back to the acid-stable, 5-methyl-folate. We might add high alpha mixed tocopherols, and tocotrienes (which, like vitamin E, come in four forms, alpha, beta, gamma and delta form). The gamma form of vitamin E (gamma-tocopherol) is particularly protective of vitamin C. Both vitamin C and E reconstitute oxidized (disulphide) glutathione back to its reduced (sulphydral) form.

Selenomethionine is a well-absorbed nutrient delivering the essential anti-oxidant Selenium to the tissues. Just as the methyl-transferases can convert methionine to S-adenosyl-methionine (SAMe), they can convert selenomethionine to adenosyl-selenomethionine, which was shown by Bremer and Natori in 1960, to be as efficient a methyl donor as S-adenosyl-methionine. For the purposes of increasing methylation in the body, Selenomethionine is useful, but only at small doses, since the preferred dose of elemental selenium is 200 mcg daily. Likewise the dose of adenosyl-selenomethionine (which is not included in this product) would be limited by potential selenium toxicity.

While these elements may be provided to the subject through diet, the subject may also ingest them in pill, powder or liquid form.

Formulations for use in the method of the invention may additionally contain compounds that provide additional health benefits to the compositions of the invention.

As one example, troxerutin, a bioflavenoid, has some impressive data supporting its role in homocysteine reduction and lowering lipids in atherosclerosis. See Olszewski, A J, et al. (1989) Atherosclerosis, 75:1-6. Rutin itself, quercetin or curcuminoids (from the tumeric or saffron family) are good alternatives.

Jiaogulan (Penta Tea, miracle grass, or Southern Ginseng) increases the HDL/LDL ration in hyperlipidemics. Jiaogulan contains triterpene saponins (gypenosides). See The Review of Natural Products by Facts and Comparisons. St. Louis, Mo.; Wolters Kluwer Co., 1999. Natural Medicines Comprehensive Database p. p. 616.

When used to treat conditions contrary to good mental health, it may be desirable, depending on the condition, to add kava kava root or extracts thereof to the formulations of the invention. Kava kava, the common name for *Piper methysticum*, is known for its calming effects and is used to treat anxiety. Kava pyrones may be supplied as the cut or dry root of the plant, as a fluid extract, or in any of the other forms well known in the art. Kava, GABA and L-taurine are anti-convulsant mood-stabilizing ingredients, which help to diminish the epileptogenic risk of 5-methyl-folate. Extracts and concentrates favoring varying ratios of the various kavalactones in the herb, kavain, dihydroxy-kavain, methysticin, dihydro-methysticin, yangonin and desmethoxy-yangonin, and others, may be chosen as to whether the inhibition of voltage-dependent sodium and/or calcium channels are desirable, or where a serotonergic-1a ($5HT_{1A}$) effect is required or where a GABA-A agonistic and an anti-glutamate action is most needed of a particular product.

Kava and GABA have anti-arrhythmic as well as anti-convulsant activity, improving the safety of the compositions of the invention, and broadening the spectrum of the population they could benefit. Anti-convulsants are particularly important because of the high blood-brain-barrier penetrance of Methyl-Folate, which can lower the seizure threshold. In addition, Kava and GABA relieve mental and somatic anxiety respectfully.

The addition of soy isoflavones is a consideration for a product designed for peri- and post-menopausal women; however there is evidence that these isoflavones may be beneficial for men as well as women. Supplemental estrogens post-menopause significantly decreases blood homocysteine while reducing the risk of coronary artery disease by as much as 50%. However, high progesterone oral contraceptives have an anti-vitamin B6 effects, associated with elevated homocysteine and increased risk of thrombosis. Soy isoflavones have a modulating effect on estrogenic activity. They have a pro-estrogenic effect in estrogen deficiency and an anti-estrogenic effect where there is estrogen excess.

Other cardioprotective factors may also be added. As one example, the compositions of the invention might be combined with natural cholesterol-lowering agents, particularly HMG reductase inhibitors (triterpene glycosides and selected saponins).

The anti-homocysteine compositions of the invention may be also combined with a specialized product for women, or for men or it may be used as the core of a system of products, including among others, an anti-aging product or a weight loss product.

Examples of Conditions Treatable with the Invention

The methods of the present invention may be used to treat any condition for which an agent that decreases homocysteine levels is indicated.

Conditions Contrary to Good Mental Health

The compositions of the invention may be used in the treatment and prevention of conditions contrary to good mental health, especially depression. As used herein, "conditions contrary to good mental health" include any psychological or organic condition that impairs normal functioning. Examples of such conditions include, but are not limited to, somatoform disorders, such as conversion disorder, hypochondria, and body dysmorphic disorder; anxiety disorders, such panic disorder, phobias, obsessive compulsive disorder, and acute stress disorder; dissociative disorders, such as dissociative amnesia, multiple personality disorder, and depersonalization disorder; mood disorders, such as depression, dysthymic disorder, bipolar disorder (bipolar I and bipolar II disorders), cyclothymic disorder; personality disorders, such as paranoia, schizoid and schizotypal personalities, borderline personality, antisocial personality, narcissistic personality, histrionic personality, dependent personality, and obsessive-compulsive personality; psychosexual disorders, such as hypoactive sexual desire disorder and sexual aversion disorder; schizophrenia and disorders related to it such as delusional disorder; and cognitive disorders of the elderly, such as Alzheimer's disease, vascular dementia, and senile dementia.

Clinical improvement has been shown in patients with cognitive impairment following treatment with vitamin B12, one of the factors known to lower homocysteine levels in the brain (Nilsson, K. et al. (2000) Aging Clin. Exp. Res. 12:199-207). Treatment with vitamin B12 and/or folate has also been shown to ameliorate both cognitive and neurological disturbances in deficient patients.

A condition need not be the kind that requires medical intervention to be considered a "condition contrary to good mental health." Depression, for example, encompasses major depressive disorder requiring aggressive treatment with antidepressant medications; it also encompasses a mild case of gloominess or "feeling blue" in response to a common stressor, such as parting with a loved one for a weekend, receiving a poor grade on an exam, or even cloudy weather. There are many ways of understanding the nature of clinical depression. (Psychosocial, learned hopelessness model, interpersonal models, psychodynamic, brain systems models, as studied by neuro-imaging and electrophysiological techniques, and psychopharmacological, which focuses on the extremely complex activities at the synapse. There, fundamentally, problems can arise from (A) the neurotransmitters (analogous to keys) and (B) the receptors (analogous to keyholes). Neuropsychiatric problems may occur if there are too many or too few active neurotransmitters, or if the receptors are too up-regulated (too sensitized or too easily engaged) or down-regulated (too desensitized or resistant to engagement). The method of the invention may be used to treat any of the foregoing conditions.

The flexibility of the receptor switching functions depends on the ability of the receptors to achieve a state of suspended balance between opposing electrochemical configurations. The addition or subtraction of methyl groups (methylation and demethylation) and phosphate groups (phosphorylation and dephosphorylation) are chief among these, but there are others (e.g., the often-reversible cross-linking of two sulphydral groups to form a disulfide bridge, as occurs in the vulcanization of rubber, also occurs in the ion channels of the brain). The on and off switches of phosphorylation and methylation are intimately linked in biochemical processes. For example the ratio of S-adenosyl-methionine to its metabolite S-adenosyl-homocysteine, normally about 1.5 (in adult rat liver), determines the degree of phosphorylation of the serine residues of the critical brain enzyme, phospholipid methyl-transferase. Imbalances between phosphorylation and dephosphorylation occur in disturbances of the neuro-endocrine and the autonomic nervous system, causing among other things disturbances in blood sugar metabolism.

The most common cause of an imbalance between methylation and demethylation is a state of hypomethylation, which is a common factor to normal aging, depression, arthritis, and a state that predisposes to carcinogenesis. The compositions of the invention are designed to address this hypomethylation, by providing compound that reduce the drain upon the methyl donor SAMe.

Associated with depression and anxiety, there is almost always an imbalance between the catabolic and anabolic processes in the body, roughly correlating with the sympathetic and the parasympathetic branches of the autonomic nervous system. The sympathetic nervous system governs "fight or flight", activation, preparation for emergencies, stresses or challenges, thickening of the blood and preparation of the clotting system of the blood to mitigate potential hemorrhage, catabolism and oxidation, temporary suspension of digestive, sexual, immunological and endocrine functions that are not immediately essential, while the parasympathetic nervous system governs "rest and repair", deactivation, thinning of the blood and anti-thrombotic activity, rest, restoration, rebuilding, anabolism and reduction or anti-oxidation.

Of the various ways that major depression can be classified or categorized there are very few that has predictive validity and reliability with respect to various treatments. The distinction between primary and secondary depression is invariably useful, as well the distinction between unipolar and bipolar depression. Both unipolar and bipolar depression can be further subdivided into an over-focused and an under-focused (or unfocused) subtype. Taking note of the presence or absence of melancholia, implying among other symptoms a severe lack of physical energy (also known as psychomotor retardation), also has predictive value as to whether or not a catechol-aminergic rather than an indole-aminergic pharmaceutical or nutraceutical medication would be likely effective. Bipolar Disorder, in the manic, depressed or mixed state, tends to be responsive to GABA'ergic medications, which are mood stabilizers, whereas the unipolar depressive disorders tend to respond to the mood elevators, i.e. the indole-aminergic (or serotonergic) agents, the catechol-aminergic (or adrenergic) agents or both. The over-focused subtype of depressive disorder (which we might call the obsessive-depressive subtype) tends to be highly responsive to the serotonergic medications, whereas the under-focused (or unfocused, or Attention Deficit Disorder (ADD)-like) subtype (which we might call the cognitively scattered subtype), is responsive (as is the melancholic subtype) to the catechol-aminergic or adrenergic pharmaceutical or nutraceutical medications or therapeutic agents. GABA'ergic, catechol-aminergic and indole-aminergic substances are available from natural sources, and may be incorporated into SAMe products, to create specific SAMe-based anti-depressants, designed to target the various subtypes of depression. Although SAMe is believed to increase turn-over of the catechol-amine, dopamine, and the indole-amine, Serotonin, the most powerful and efficacious action of SAMe is believed to be the increased fluidity of the post-synaptic membrane, upon which the chemical messengers, known as neurotransmitters act. Long-term adaptive adjustments of the receptivity of this membrane are widely believed to be the critical neurophysiological events that promote and maintain good neuropsychiatric health.

When used to treat conditions contrary to good mental health, it may be desirable, depending on the condition, to add kava kava root or extracts thereof to the formulations of the invention. Kava kava, the common name for *Piper methysticum*, is known for its calming effects and is used to treat anxiety. Kava pyrones may be supplied as the cut or dry root of the plant, as a fluid extract, or in any of the other forms well known in the art.

Heart and Cerebrovascular Disorders:

The methods of the invention may be used to treat or prevent a heart disorder such as congestive heart failure, ischemic heart disease, angina pectoris, myocardial infarction, hypertensive heart disease, degenerative valvular heart disease, calcific valve stenosis, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease and congenital heart disease; and a cerbrovascular disease such as arteriovenous fistula, atherosclerois, atherothrombosis, hypertension, vasculitis, Raynaud's disease, aneurysms, arterial dissections, varicose veins, thrombophlebitis and phlebothrombosis, vascular tumors, and vascular dementia.

Anti-homocysteine agents have been used to treat cardiovascular disorders such as atherothrombotic cerebrovascular disease (Verneulen, E. G. et al., (2000) Neth. J. Med. 56:138-146).

Renal Disorders:

The method of the invention may also be used to treat and prevent renal disorders, including but not limited to renal amyloidosis, hypertension, primary aldosteronism, Addison's disease, renal failure, glomerulonepritis, chronic glomerulonepritis, tubulointerstitial nepritis, cystic disorders of the kidney, polycystic disease, renal dysplasias, cortical or medullary cysts, Alport's syndrome, and inherited polycystic kidney diseases.

Alcoholism and Liver Disorders.

The method of the invention may also be used to treat and prevent liver dysfunction. The term "liver dysfunction," as used herein, refers to any condition which impairs normal functioning of the liver. It includes, but is not limited to, conditions such as hepatomegaly, portal hypertension, portal-systemic encephalopathy, hepatic steatosis, fibrosis, cirrhosis, particularly alcohol-induced cirrhosis, hepatitis, hepatocellular necrosis, hepatic granulomas, hepatic cysts, and tumors of the liver, such as hepatocellular adenoma. The method of the invention may be used to treat liver dysfunction and conditions secondary to it, such as jaundice, disorders of bilirubin metabolism, and cholelithiasis.

The compositions of the invention are potentially valuable as a hepatoprotective supplement in cases of ongoing alcohol and polysubstance abuse. SAMe is hepatoprotective through various mechanisms, including methylation, sulfation and generation of the anti-oxidant, glutathione and this product in particular has homocysteine-lowering components. The excitatory amino acid, homocysteine and its metabolites act as agonists at the N-methyl-D-aspartate (NMDA) receptor. Over-stimulation of this NMDA receptor is believed to mediate the neuronal excitotoxicity, that predominates as the cause of neurotoxicity. Recent MRI studies from Germany correlate high homocysteine plasma levels with reduced brain hippocampal volume in chronic alcoholics. The effect was greater in the women in the study, who also had low folate, vitamin B6 and significantly high homocysteine compared to non-drinking controls. Alcohol-induced hyper-homocysteinuria is believed to be part of the mechanism of brain damage in alcoholics. Whether this occurs by the induction of low glucose tolerance, or deficiency of folate or other B Complex vitamins is yet unclear.

Obesity and Blood Sugar Disturbances:

Diabetes type II is occurring co-morbidly with obesity, with greater and greater frequency, especially in younger people. Diabetes is often accompanied by vascular and neurological complications. Significantly elevated levels of homocysteine have been observed in type II diabetes patients with vascular complications (Araki, A. et al. 1993).

When used to produce a weight-reducing product, it may be desirable to add a source of methylxanthines, such as Guarana or Ephedra to the present invention. As discussed above, methylxanthines, such as caffeine and theophylline, function as phosphodiesterase inhibitors. Their activity results in less cAMP being converted to AMP, so that more cAMP is available to activate protein kinase, which would then phosphorylate a substrate protein (e.g. an ion channel or an enzyme), to obtain a biological response at that receptor. These methylxanthines block the purinoceptor P1, (where adenosine is the endogenous ligand), and thereby reducing it's inhibitory effect of locomotion, mental activation and post-synaptic hyper-polarization. The co-administration of one or more of the adaptogens, *Panax Ginseng*, Siberian Ginseng (*Eleutherococcus senticosis*), and other adaptogens, such as *Schizandra chinensis, Withania somnifera* (Ashwaganda root) or *Cordiceps sinensis* adds to the energy enhancing effect of proprietary SAMe as well as the present invention.

Hyper-estrogen States and Prevention of Gynecological Malignancies

For control of hyper-estrogen states, and for the prevention of gynecological malignancies, the compositions of the present invention may be combined with other ingredients known to be beneficial for hyper-estrogen states. These would include flax seed oil for aromatase inhibitor activity, Omega-3 FFAs, Calcium-D-Glutarate, alternative estrogen-modulating isoflavones and other phytoestrogens (e.g. lignans, Red Clover), Indole-3-Carbinol (,I3C), black cohosh, chasteberry, ginseng, dong quai, licorice, limonene and Resveratrol. (grape skin extract)

Anabolism, Bodybuilding and Healing:

Guanidoacetic acid is methylated to creatine in the liver. There is an impressive body of evidence showing the anabolic benefits of creatine in body-building and in body healing. Since the absence of adequate methylation is the biggest barrier to the body's endogenous production of this beneficial body nutrient, the compositions of our invention, which improve methylation, would render the exogenous supplementation of creatine unnecessary. Hence our claims that this product has value in body-building and wound-healing (in various situations, e.g. post-trauma or post-surgical).

The method of the invention may also be used to prevent tooth loss, facilitate lactation in pregnant women, to decrease menopausally-related sleep disturbances and other forms of insomnia, to improve the performance of athletic athletes, to improve memory, treat migraines, to treat neurodegenerative diseases such as multiple sclerosis (by repairing myelin), alleviate caffeine craving, promote the healing of ulcers, increase the effectiveness of cold medications (including herbal preparations such as *Echinacea*). The method may also be used to increase the effectiveness of prescription antidepressants.

Anti-Aging and Memory Preservation:
Memory Problems:

Clinical improvement has been shown in patients with cognitive impairment following treatment with vitamin B12, one of the factors known to lower homocysteine levels in the brain (Nilsson, K. et al. (2000) Aging Clin. Exp. Res. 12:199-207). Treatment with vitamin B12 and/or folate has also been shown to ameliorate both cognitive and neurological disturbances in deficient patients.

SAMe induces phospholipid methylation, improving membrane fluidity and micro-viscosity, and notably improving or reversing the age-related decrease in binding sites in beta-adrenergic receptors.

Chronic administration of SAMe to rats prevents the age-related decrease in beta-adrenergic binding sites and the age-related decrease of brain membrane fluidity, probably on the basis of its effect on phospholipid methylation.

Phenylethanolamine gets methylated by SAMe to Phosphatidylserine, which gets further methylated to Phosphatidylcholine, which is probably cleaved by the hydrolylases to be a source of the intercellular neurotransmitter, acetylcholine. Substances that increase methylation, such as folate, increase acetylcholine, which is needed to reverse cognitive decline and memory disturbances in conditions such as Alzheimer's Disorder.

Anti-Aging and Cancer-Prevention:

In creating a safe methylating product, an important problem to be solved is to create a product that would promote the growth of healthy tissues without also promoting the growth of neoplasms or cancerous tissue. In other words it should be anabolic but not carcinogenic.

An abnormal build up of polyamines are suspected of being part of the mechanism of accelerating cancer growth once it has occurred.

Safety factors, such as the inclusion of soy isoflavones, allow for an anti-estrogenic effect when the estrogen levels are too high, and a pro-estrogenic effect when the estrogen levels are too low.

Since a state of under-methylation or 'hypo-methylation' is associated with an increased propensity towards carcinogenesis, the compositions of the invention, which encourage methylation, have a built-in safety mechanism.

These compositions of the invention create a drain for homocysteine, and increase the ratio of S-adenosyl-methionine to S-adenosyl-homocysteine, which is a significant inhibitor of methylation.

In addition to the active ingredients described herein, formulations according to the invention may optionally contain one or more excipients, including the following: preservatives, such as ethyl-p-hydroxybenzoate; suspending agents such as methyl cellulose, tragacanth, and sodium alginate; wetting agents such as lecithin, polyoxyethylene stearate, and polyoxyethylene sorbitan mono-oleate; granulating and disintegrating agents such as starch and alginic acid; binding agents such as starch, gelatin, and acacia; lubricating agents such as magnesium stearate, stearic acid, and talc; and flavoring and coloring agents.

Formulations of the present invention suitable for oral administration may be presented in any of the following forms: discrete units such as capsules, cachets, or tablets each containing a predetermined amount of the active ingredient; powder or granules; solutions or suspensions in an aqueous liquid or a non-aqueous liquid; or, as oil-in-water liquid emulsions or water-in-oil emulsions, and any other form suitable for oral administration.

In one alternative embodiment, the formulation is contained within a food stuff, such as a cookie, a bar of chocolate, a gum or jelly (e.g., a gummy bear), or a yogurt. It may similarly be contained in a nutrition bar, energy bar or a meal replacement bar. The formulation may be added to an egg mix to counteract the high content of cholesterol and saturated fats found in eggs. The formulation may also be added to coffee creamer (for use with decaffeinated coffee or tea) to relieve caffeine craving and to mitigate the effects of aluminum silicate commonly found in creamers.

In still further embodiments, the formulation may be added to an antacid preparation such as those containing sodium bicarbonate, aluminum hydroxide, or magnesium hydroxide. The formulation promotes methylation of DNA in the stomach, prevents stomach and gastrointestinal cancers, and promotes the healing of ulcers.

Formulations for rectal administration may be presented as a suppository with a suitable base comprising, for example, cocoa butter or a salicylate.

Formulations suitable for nasal administration may comprise either solid or liquid preparations. Where the carrier is a solid, it may be a coarse powder having a particle size, for example, in the range of 20 to 500 microns. This powder is administered in the manner in which snuff is taken, i.e., by rapid inhalation through the nasal passage from a container of the powder held close up to the nose. Where the carrier is a liquid, it may be administered as a nasal spray or as nasal drops.

Formulations suitable for vaginal administration may be presented as pessaries, tampons, creams, gels, pastes, foams, or spray formulations.

Formulations suitable for parenteral administration include, for example, aqueous and non-aqueous sterile injection solutions, which may contain anti-oxidants, buffers, bacteriostats, and solutes, which render the formulation isotonic with the blood of the intended recipient; and aqueous and non-aqueous sterile suspensions which may include suspending agents and thickening agents. The formulations may be presented, for example, in unit-dose or multi-dose containers, sealed ampules and vials, and may be stored in freeze-dried (lyophilized) conditions requiring only the addition of the sterile liquid carrier immediately prior to use.

In one embodiment of the invention, a subject ingests during one part of the day, such as the morning, a first formulation containing 5M-THF, methylcobalamin and one or more of betaine, P5P, and N-acetyl-cysteine, and ingests during another part of the day, such as the evening, a second formulation containing co-factors (or mostly co-factors).

While the invention has been described in connection with specific exemplary embodiments, it will be apparent to those skilled in the art that various changes can be made to the structure, arrangement, proportions, elements, and materials used in the practice of the invention without departing from its principles.

What is claimed is:

1. A composition for promoting the decrease of homocysteine within a human, comprising 5-methyl tetrahydrofolate, methylcobalamin, one or more compounds selected from the group consisting of betaine, pyridoxal-5-phosphate, and N-acetyl-cysteine, and one or more compounds selected from the group consisting of Rhodiola Rosea, GABA, kava kava, troxerutin, rutin, quercetin, Jiangulan and HMG reductase inhibitors.

2. The composition of claim 1, wherein the composition comprises betaine, pyridoxal-5-phosphate, and N-acetyl-cysteine.

3. The composition of claim 1, wherein the composition further comprises intrinsic factor.

4. The composition of claim 1, wherein the composition further comprises one or more compounds selected from the group consisting of alpha-lipoic acid, choline bitartrate, coenzyme Q10, L-taurine, piperine, selenomethionine, one or more B vitamins, vitamin A, vitamin C, Vitamin E, and zinc methionate.

5. The composition of claim 1, wherein the composition further comprises soy isoflavones.

6. The composition of claim 1, wherein the composition further comprises one or more compounds selected from the group consisting of folate and cyanocobalamin, wherein the ratio of folate to 5M-THF is between about 5:1 to about 50:1 by weight and wherein the ratio of cyanocobalamin to methylcobalamin is between about 5:1 to about 50:1 by weight.

7. The composition of claim 1, wherein the composition further comprises one or more compounds selected from the group consisting of folate and cyanocobalamin, wherein the ratio of folate to 5M-THF is about 10:1 by weight and wherein the ratio of cyanocobalamin to methylcobalamin is about 10:1 by weight.

8. The composition of claim 1, wherein the composition further comprises one or more compounds selected from the group of guarana and ephedra.

9. The composition of claim 1, wherein the composition further comprises calcium and magnesium in a ratio of about 1:2 to about 2:1 by weight.

10. The composition of claim 1, wherein the composition further comprises an excipient.

11. A composition for promoting the decrease of homocysteine within a human, comprising 5-methyl tetrahydrofolate, methylcobalamin, betaine, pyridoxal-5-phosphate, N-acetyl-cysteine, and one or more compounds selected from the group consisting of Rhodiola Rosea, GABA, kava kava, troxerutin, rutin, quercetin, Jiangulan and HMG reductase inhibitors.

12. A method of treating increased levels of homocysteine in a human, comprising administering to the human a formulation comprising 5-methyl tetrahydrofolate, methylcobalamin, one or more compounds selected from the group consisting of betaine, pyridoxal-5-phosphate, and N-acetyl-cysteine, and one or more compounds selected from the group consisting of Rhodiola Rosea, GABA, kava kava, troxerutin, rutin, quercetin, Jiangulan and HMG reductase inhibitors.

13. The method of claim 12, wherein the formulation is administered via oral administration.

14. The method of claim 12, wherein the formulation is presented in a form selected from the group consisting of capsule, cachets and tablets.

15. The method of claim 12, wherein the formulation is administered in a form selected from the group consisting of pill, powder and liquid.

16. The method of claim 12, wherein the formulation is contained within a food stuff.

17. The method of claim 12, wherein the formulation is administered to the human such that the daily dose of 5M-THF is from about 10 mg to about 1000 mg and the daily dose of methylcobalamin is from about 10 mg to about 1000 mg.

18. The method of claim 12, wherein the formulation is administered to the human such that the daily dose of 5M-THF is about 100 mg and the daily dose of methylcobalamin is about 100 mg.

19. The method of claim 12, wherein the formulation is administered to the human such that the daily dose of L-methionine is about 2,500 mg.

20. The method of claim 12, wherein the formulation is administered to the human in 2-4 doses per day.

21. The method of claim 12, wherein the formulation comprises 5-methyl tetrahydrofolate, methylcobalamin, betaine, pyridoxal-5-phosphate, and N-acetyl-cysteine.

22. The method of claim 12, wherein the formulation further comprises intrinsic factor.

23. The method of claim 12, wherein the formulation further comprises one or more compounds selected from the group consisting of alpha-lipoic acid, choline bitartrate, coenzyme Q10, L-taurine, piperine, selenomethionine, one or more B vitamins, vitamin A, vitamin C, Vitamin E, and zinc methionate.

24. The method of claim 12, wherein the formulation further comprises soy isoflavones.

25. The method of claim 12, wherein the formulation further comprises one or more compounds selected from the group consisting of folate and cyanocobalamin, wherein the ratio of folate to 5M-THF is between about 5:1 to about 50:1 by weight and wherein the ratio of cyanocobalamin to methylcobalamin is between about 5:1 to about 50:1 by weight.

26. The method of claim 12, wherein the formulation further comprises one or more compounds selected from the group consisting of folate and cyanocobalamin, wherein the ratio of folate to 5M-THF is about 10:1 by weight and wherein the ratio of cyanocobalamin to methylcobalamin is about 10:1 by weight.

27. The method of claim 12, wherein the formulation further comprises calcium and magnesium in a ratio of about 1:2 to about 2:1 by weight.

28. A method of treating and preventing diseases selected from the group consisting of conditions contrary to good mental health, heart diseases, cerebrovascular diseases, and renal disorders, comprising administering to a human a formulation comprising 5-methyl tetrahydrofolate, methylcobalamin, one or more compounds selected from the group consisting of betaine, pyridoxal-5-phosphate, and N-acetyl-cysteine, and one or more compounds selected from the group consisting of Rhodiola Rosea, GABA, kava kava, troxerutin, rutin, quercetin, Jiangulan and HMG reductase inhibitors.

29. A method of decreasing homocysteine in a human having a genetic condition related to homocysteine levels in the body, comprising administering to the human a formulation comprising 5-methyl tetrahydrofolate, methylcobalamin, one or more compounds selected from the group consisting of betaine, pyridoxal-5-phosphate, and N-acetyl-cysteine, and one or more compounds selected from the group consisting of Rhodiola Rosea, GABA, kava kava, troxerutin, rutin, quercetin, Jiangulan and HMG reductase inhibitors.

30. A method of decreasing homocysteine in a human comprising:
administering during a first half of a day a first formulation comprising 5-methyl tetrahydrofolate, methylcobalamin, and one or more of betaine, pyridoxal-5-phosphate and N-acetyl-cysteine, and one or more compounds selected from the group consisting of Rhodiola Rosea, GABA, kava kava, troxerutin, rutin, quercetin, Jiangulan and HMG reductase inhibitors; and administering during a second half of a day a second formulation comprising alpha lipoic acid, choline bitartate, coenzyme Q10, L-taurine, piperine, selenomethionine, one or more B vitamins, vitamin A, vitamin C, vitamin E, and zinc methionate.

* * * * *